(12) United States Patent
Irion et al.

(10) Patent No.: US 6,364,827 B1
(45) Date of Patent: Apr. 2, 2002

(54) ENDOSCOPE WITH AT LEAST ONE SENSING AND RECORDING DEVICE

(75) Inventors: Klaus Irion, Emmingen-Liptingen; Jürgen Rudischhauser, Tuttlingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/230,667

(22) PCT Filed: Jul. 29, 1997

(86) PCT No.: PCT/DE97/01604

§ 371 Date: Mar. 29, 1999

§ 102(e) Date: Mar. 29, 1999

(87) PCT Pub. No.: WO98/04185

PCT Pub. Date: Feb. 5, 1998

(30) Foreign Application Priority Data

Jul. 29, 1996 (DE) .......................................... 196 30 635
Jun. 4, 1997 (DE) .......................................... 197 23 442

(51) Int. Cl.⁷ ................................................ A61B 1/00
(52) U.S. Cl. ...................................... 600/118; 600/117
(58) Field of Search ................................ 600/103, 109, 600/117, 118, 162; 348/65, 74, 76

(56) References Cited

U.S. PATENT DOCUMENTS

| 4,996,975 A | * | 3/1991 | Nakamura | .................. 600/118 |
|---|---|---|---|---|
| 4,998,282 A | * | 3/1991 | Shishido et al. | ............. 600/117 |
| 5,031,454 A | * | 7/1991 | Ams | .......................... 73/336.5 |
| 5,301,061 A | * | 4/1994 | Nakada et al. | ............... 600/121 |
| 5,337,732 A | | 8/1994 | Grundfest et al. | |
| 5,402,769 A | * | 4/1995 | Tsuji | ........................... 600/118 |
| 5,421,821 A | | 6/1995 | Janicki et al. | |
| 5,571,133 A | | 11/1996 | Yoon | |
| 5,604,531 A | * | 2/1997 | Iddan et al. | ................. 600/109 |
| 5,800,341 A | * | 9/1998 | McKenna et al. | ........... 600/109 |

FOREIGN PATENT DOCUMENTS

| DE | 37 41 879 A1 | 6/1988 |
|---|---|---|
| DE | 37 07 787 A1 | 9/1988 |
| DE | 195 22 909 A1 | 1/1997 |
| EP | 0 561 228 A2 | 9/1993 |
| JP | 58221820 A | * 12/1983 |
| JP | 01284226 A | * 11/1989 |
| JP | 04102431 A | * 4/1992 |
| WO | WO 90/04358 | 5/1990 |
| WO | WO 94/14129 | 6/1994 |

* cited by examiner

Primary Examiner—John P. Leubecker
(74) Attorney, Agent, or Firm—St. Ogne Steward Johnston & Reens LLC

(57) ABSTRACT

An endoscope comprising at least one sensing and recording device disposed in the interior of the endoscope, which detects at least one ambient parameter such as temperature, pressure, humidity, irradiation, other ambient conditions and/or shock or impact loads which the endoscope is exposed to, where the information recorded by the sensing and recording device may be extracted from the outside or transmitted to the outside of the endoscope without disassembly of the endoscope.

10 Claims, 2 Drawing Sheets

ENDOSCOPE WITH AT LEAST ONE SENSING AND RECORDING DEVICE

FIELD OF THE INVENTION

The present invention relates to an endoscope comprising a distally disposed lens and an image transmission system which transmits the image from the lens to the proximal end.

PRIOR ART

Endoscopes of this kind are commonly known and are used, for instance, in medicine or engineering applications for observing cavities, particularly under aggravated conditions.

The image transmission system may consist of one or several distally disposed semiconductor chips such as CCD elements, a relay lens system preferably including rod lenses or a fibre bundle.

In operation and/or during cleaning or sterilisation the endoscopes are frequently exposed to elevated temperatures—up to 140° C. when they are sterilised by autoclave—pressures and/or aggressive media—e.g. when they are sterilised in solutions. Depending on their design the endoscopes are specified only up to defined ambient conditions. When these limits are exceeded the most different types of damage may occur:

As a result of improper handling temperatures and/or pressures may occur which are above the admissible limits. As a consequence, joints such as the connection between the distal terminal window of the lens and the outside tube may be damaged so that the endoscope is no longer fluid tight and humidity can penetrate into the interior. In endoscopes with a semiconductor chip this chip may be destroyed by excessively high temperatures. Similar conditions prevail when the endoscope is exposed to other ambient conditions for which it is not specified, and/or to the action of aggressive media.

Moreover, specifically the elongate introducing elements of the endoscopes may be exposed to shocks or impacts when they are not carefully handled. This may easily result in damage, e.g. on rod lenses, particularly in breaking. Even if no lenses are broken, the endoscope might be misadjusted.

The operator frequently does not even note that the endoscope is employed beyond the specified conditions. This leads not only in unjustified complaints versus the endoscope manufacturer but results also in sudden failure of the endoscope during application or causes other damage induced by the endoscope.

BRIEF DESCRIPTION OF THE INVENTION

The present invention is based on the problem of improving an endoscope of the claimed general type in a way that particularly operating conditions beyond the specified range can be recognised.

In accordance with the invention the endoscope comprises at least one sensing and recording device disposed in the interior of the endoscope, which detects the particular temperatures, pressure, humidity, irradiation, ambient conditions and/or shock or impact loads which the endoscope is exposed to.

The sensing and recording device which is provided in accordance with the invention and integrated into the endoscope permits the detection of the history of this endoscope so that the causes of failure etc. can be reconstructed.

Moreover, the information recorded or stored by the sensing and recording device, which refers to the history can be extracted from the outside without disassembly of the endoscope. An operator can hence recognize at any time whether the endoscope has been exposed to unacceptable ambient conditions in the past. This enables the operator in particular to screen an endoscope involving a high probability of failure on account of its history before failure of the endoscope occurs—e.g. during a surgical operation.

The sensing and recording device provided and configured in accordance with the invention has hence a checking function which allows for endoscope monitoring.

The extraction from the outside may take place either by the fact that the sensing and recording device is visible through a window in the endoscope or that the stored information is transmitted to the outside e.g. electrically and particularly without contact.

The sensing and recording device is preferably so configured that it detects and stores the maximum value occurring in each case or, in an alternative or additionally, counts or stores the number of critical situations or states.

The term critical situations or states is to be understood here to denote conditions in which the permissible maximum values are exceeded for the individual parameters such as temperature, pressure, etc.

On principle any means whatsoever may be used as sensing and recording device, which comprise, for instance, mechanical indicators and/or electronic sensors, on the condition that these means are only able to detect the occurring values of the respective ambient condition and to store at least the peak value.

A particularly simple configuration of the sensing and recording device for detection of the occurring temperature or humidity comprises a color indicator element which signals the temperature or humidity value by its color. The change of color is preferably irreversible so that the maximum temperature, for instance, to which the endoscope had been exposed, can be reliably established even subsequently.

The sensing and recording device comprises a membrane which closes a small space isolated from the interior proper of the endoscope, where air is contained under normal pressure, and which breaks at a specified pressure difference between the environment and the small space.

The sensing and recording device for the detection of shock or impact loads also comprises a break-off element, which breaks at a specified load.

It is preferable—as has been set out in the foregoing—to provide for external extraction of the information recorded or stored by the sensing and recording device without disassembly of the endoscope it is preferred that at least one of the indicators of the sensing and recording device is visible from the outside. To this end, the indicator or indicators of the sensing and recording device in the endoscope may be disposed behind a window so that they are visible from the outside. This window is preferably the lens window of the endoscope so that it is not necessary to leave an additional window open in the outside wall of the endoscope.

As has been set out in the foregoing, it is possible to use also electronic sensors in addition to the aforementioned mechanical sensors or indicators operative by change of colour.

It is, of course, also possible that the sensing and recording device comprises at least one sensor—instead of or additionally to the aforementioned indicator elements indicating by change of color or mechanically that a limit has been exceeded—for electronically detecting the specific temperature, pressure, humidity, irradiation, other ambient conditions or shock or impact loads which the respective endoscope had been exposed to. To this end the endoscope comprises an energy accumulator, a sensor detecting one of these parameters and converting it into an electrical signal, as well as a signal processing unit which is capable of performing a preliminary processing of the parameters and storing in particular the deviation beyond parameters. Moreover, a transmitter unit is provided for transmitting the stored information to the outside.

It is furthermore preferred that the sensing and recording device additionally includes a timer system so that the time of occurrence of a critical state will be detected and output in combination with the detected parameters. With these provisions it is possible, for instance, to associate improper handling of an endoscope with an identified user.

This transmitter unit may be a plug, however a wireless system is preferred which may be configured in particular in the manner of a telemetric system.

It is moreover preferred, that the energy accumulator can also be charged from the outside—via plug or, equally preferably, without contact—because in such a case it is not necessary to open the endoscope for maintenance of the sensing and recording device.

When the sensing and recording device is configured as electronically operating sensing and recording device, as has been set out in the foregoing, it is furthermore preferred that, the sensing and recording device performs recognition of further events only upon the lapse of a certain predetermined interval when certain temperature and pressure thresholds are exceeded. With this provision it is possible in particular that the sensing and recording device detects the number of sterilization cycles which are then weighted in correspondence with their respective duration.

It is moreover expedient that the receiver means be so configured that it receives the signals from a plurality of sensing and recording device. To this end each sensing and recording device transmits an unambiguous identification of the respective end, and particularly the deviation beyond set parameters, separately for each endoscope.

In the improvement of the invention according to claim 19 the sensing and recording device detects or records additionally also the functional parameters of the endoscope, such as the position of a zoom or variable lens, the position of an endoscope-internal sensing and recording system, etc.

BRIEF DESCRIPTION OF THE DRAWINGS

Furthermore, these types of sensors 4 can also include a pressure sensor, which comprises a membrane that closes a small space isolated from the interior proper of the endoscope where air is contained under normal pressure. FIG. 1a depicts such a pressure detector. P illustrates an environmental pressure. P1 illustrates a pressure P1 exerted upon the outer face of the pressure detector. P2 illustrates the pressure inside the pressure detector. At a specified pressure differential between the pressure exerted on the outside of the pressure detector and the pressure inside the pressure detector, the membrane located within the pressure detector breaks thereby registering at least a minimum pressure differential, namely the level at which the differential pressure breaks the membrane.

DESCRIPTION OF AN EMBODIMENT

Figure 1:
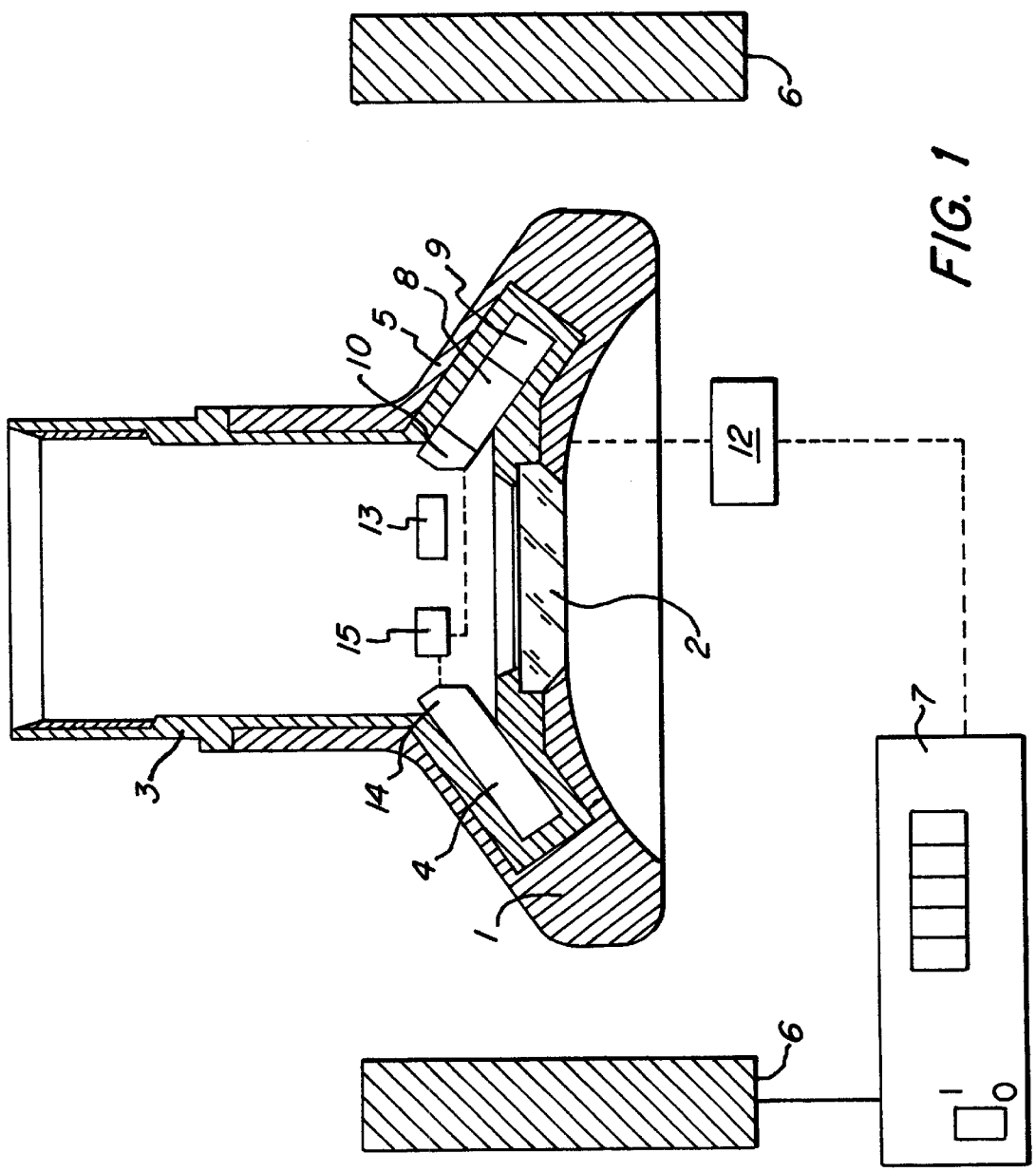
FIG. 1 shows a longitudinal section taken through the proximal section of an endoscope and a receiver means.
Figure 1A:
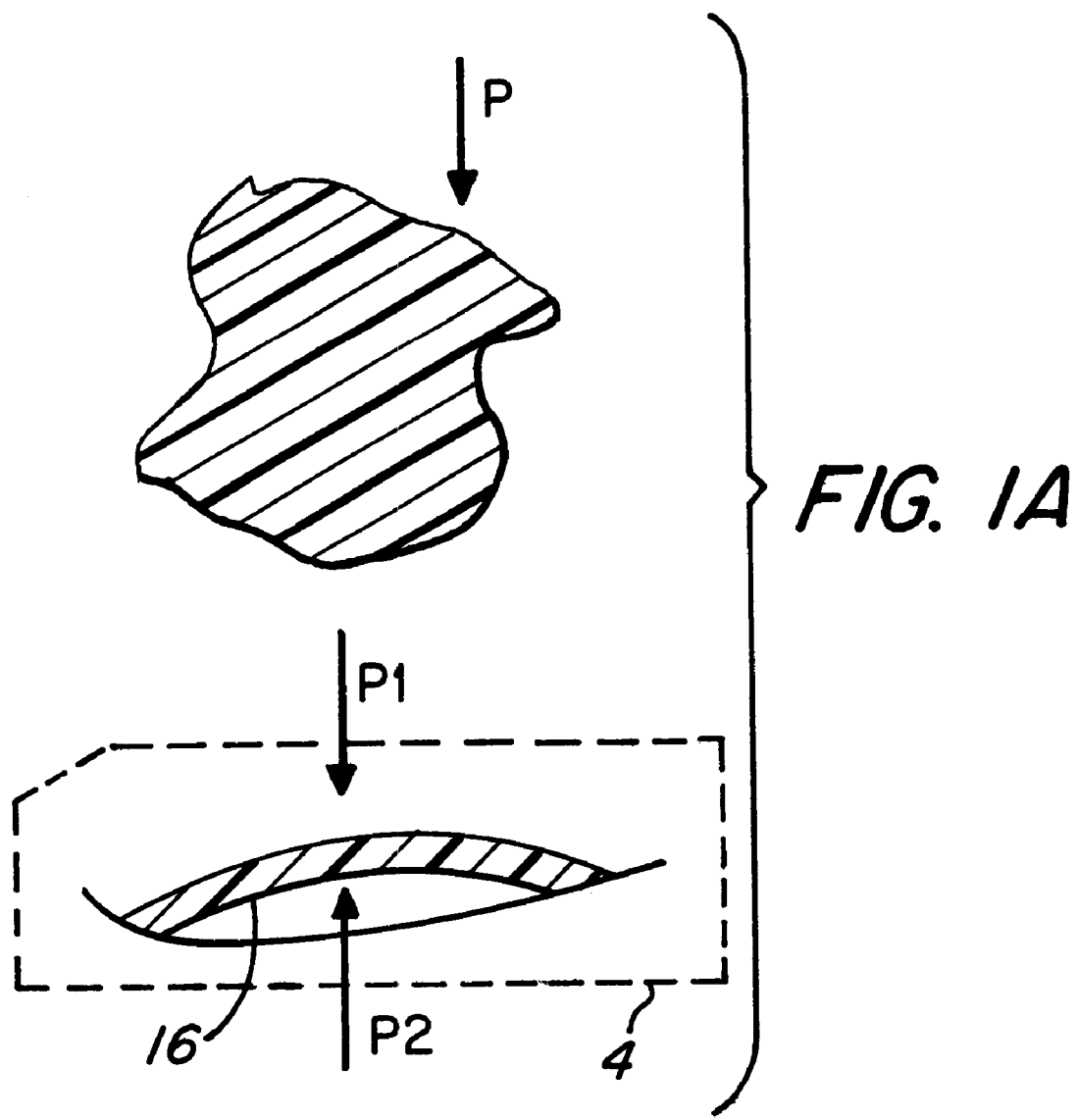
FIG. 1a illustrates a pressure detector.

In the drawing the proximal section of an endoscope is illustrated, i.e. an eyepiece cup 1 with an eyepiece window 2. The eyepiece cup 1 is joined by the proximal section of the endoscope on which the fibre-optical light guide connector is disposed which is not illustrated in the drawing.

In the region of the eyepiece cup 1 elements 4 and 5 of a sensing and recording device are shown.

The element 4 is an indicator element which indicates, for example, the maximum temperature occurring in the interior of the endoscope or the humidity by change of colour. The element 4 can here be viewed through the eyepiece window 2.

Without any restriction of the general applicability, the element 5 is an electronic sensor means which comprises an energy accumulator 10 which may be charged from the outside on the telemetry principle, a sensor 9 which detects a critical parameter such as temperature, pressure, humidity, irradiation, acceleration, etc. and converts it into an electrical signal, as well as signal pre-processing unit 13.

Moreover, a transmitter element 8 is integrated as transmitter means which is equally capable of operating on the principle of telemetry and modulation of a wave field irradiated from the outside through the transmitter unit for minimization of the power required for transmission.

The reference numeral 6 denotes an antenna for the radiated signal. The output signal of the antenna 6 is applied to an electronic receiver and analyzer means 7 which receives the signal output from the sensor unit 5 and an unambiguous system identifier characteristic of the respective endoscope. The system identifier may consist in particular of a serial number of the endoscope, the endoscope type and the date of manufacture. The receiver and analyzer means stores the individual parameters with assignment for system identification so that it is possible to extract the individual values, and particularly the deviations beyond parameters, for each endoscope separately.

Thus, the endoscope can have a structure provided with mechanically operated sensors 4 which change their physical state in response to certain ambient changes. Particularly, temperature and humidity sensors include a color indicator element which signals the temperature or humidity value by its color. The change of color is preferably irreversible so that the maximum temperature, for instance, to which the endoscope had been exposed, can be reliably established even subsequently.

To detect shock or impact loads, the sensor 4 comprises a break-off element which breaks at a specified load.

These sensors not only indicate the critical changes of the ambient environment, but they also are visible through the eyepiece window 2. Therefore, these sensors are able to store the effects of the critical conditions until a person responsible for maintenance of the endoscope will notice the change.

In addition to sensors 4 or alternatively, the endoscope can be provided with sensors 9 generating an electrical signal in response to detecting a peak value of the above disclosed parameters. This signal may be stored in the pre-processing unit 13 and later retrieved by the electronic receiver and analyzer means 7. As mentioned before, the sensor unit is in a wireless communication mode with the analyzer means 7 by means of antenna 6. Alternatively, the sensor unit can be connected to the analyzer means by a plug 12.

What is claimed is:

1. An endoscope having a distal and a proximal end comprising:
   a lens disposed at the distal end of the endoscope;
   an image transmission system which transmits an image from the lens to the proximal end of the endoscope;

a sensing device disposed within the endoscope, which detects a peak value exceeding a permissible maximum value of at least one ambient parameter selected from the group comprising temperature, pressure, humidity, irradiation, shock, impact and combinations of these which the endoscope is exposed to, and which indicates the detected peak value of the detected parameter outside the endoscope;

a recording device located in the endoscope and storing the detected peak value as a stored data; and a transmitter system transmitting the stored data outside the endoscope without contact into the environment and without disassembly of the endoscope wherein the recording device stores and counts a number of detections of the peak value.

2. The endoscope according to claim 1, wherein the sensing device is a break-off means indicating the peak value of shock or impact loads, which breaks at the peak value exceeding the permissible maximum load.

3. The endoscope according to claim 1, wherein the sensing device comprises:

at least one energy accumulator;

a sensor, which converts the peak value of the detected parameter into an electrical signal;

a signal preprocessing unit; wherein the transmitter system transmits the preprocessed signal to a receiver means located outside the endoscope.

4. The endoscope according to claim 3, wherein at least one of the sensing device and the recording device includes a timer system so that the time of occurrence of a critical state is detected and output with allocation to the detected parameters.

5. The endoscope according to claim 3, wherein the transmitter system is configured for wireless transmission of the information.

6. The endoscope according to claim 3, wherein the signal pre-processing unit stores the peak value after the lapse of a predetermined interval of time within which a parameter selected from the group consisting of temperature and pressure thresholds are exceeded.

7. The endoscope according to claim 3, wherein the energy accumulator is adapted for being charged from outside the endoscope.

8. The endoscope according to claim 3, wherein the recording device transmits the stored data and identification information relating to the respective endoscope including, an endoscope serial number, an endoscope type and a date of manufacture.

9. The endoscope according to claim 8, wherein the recording device is configured to receive signals from a plurality of sensing devices.

10. The endoscope according to claim 3, wherein the recording device stores the individual parameters with allocation to a system identification.

\* \* \* \* \*